United States Patent

Hall et al.

[11] Patent Number: 5,362,888
[45] Date of Patent: Nov. 8, 1994

[54] PREPARATION OF POLYCYCLIC DYES

[75] Inventors: Nigel Hall, Bury; Michael C. H. Standen, Clackmannan, both of United Kingdom

[73] Assignee: Zeneca Limited, London, United Kingdom

[21] Appl. No.: 76,197

[22] Filed: Jun. 14, 1993

[30] Foreign Application Priority Data

Jun. 15, 1992 [GB] United Kingdom ............. 9212629

[51] Int. Cl.$^5$ ................ C07D 307/80; C07D 307/81
[52] U.S. Cl. .................................. 549/299
[58] Field of Search ........................ 549/299

[56] References Cited

U.S. PATENT DOCUMENTS 4,680,417  7/1987  Kenyon et al. .................. 549/299

FOREIGN PATENT DOCUMENTS 363034  11/1990  European Pat. Off. .
450765  10/1991  European Pat. Off. .
502278   9/1992  European Pat. Off. .
2103231A 2/1983  United Kingdom ............. 549/299

OTHER PUBLICATIONS

Bayer et al., "Darstellung und Eigenschaften mesoionisher Oxazolone", Chemische Berichte, 1970, vol. 103, pp. 2581–2597.

Primary Examiner—C. Warren Ivy
Assistant Examiner—Ba K. Trinh
Attorney, Agent, or Firm—Cushman, Darby & Cushman

[57] ABSTRACT

A process for the preparation of a polycyclic dye of Formula (1):

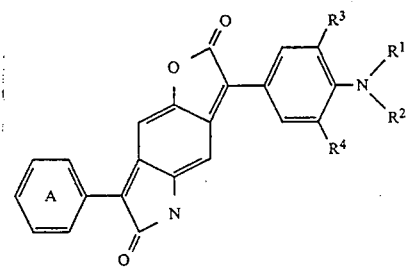

Formula (1)

by reacting a compound of Formula (2):

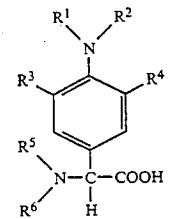

Formula (2)

with a benzofuranone of Formula (3):

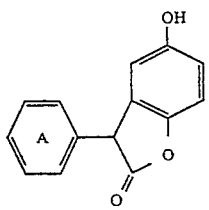

Formula (3)

wherein:
  $R^1$ and $R^2$ each independently is —H or alkyl;
  $R^3$ is alkyl;
  $R^4$ is —H or alkyl;
  $R^5$ and $R^6$ each independently is alkyl; or
  $R^5$ and $R^6$ together with the N atom to which they are attached form a heteroalicyclic ring; and
  Ring A is unsubstituted or is substituted by from one to three substituents provided that at least one of $R^1$, $R^2$ and $R^4$ is —H.

The polycyclic dyes of Formula (1) are useful for the coloration of synthetic textiles such as polyester to which they impart blue to navy shades.

1 Claim, No Drawings

PREPARATION OF POLYCYCLIC DYES

This invention relates to a process for preparing polycyclic dyes and to novel intermediates used in the process.

According to the present invention there is provided a process for the preparation of a polycyclic dye of Formula (1):

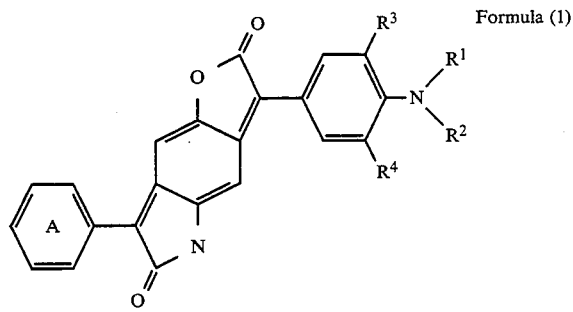

by reacting a compound of Formula (2):

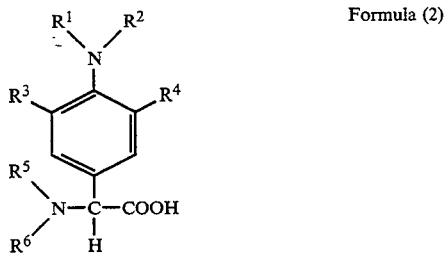

with a benzofuranone of Formula )3):

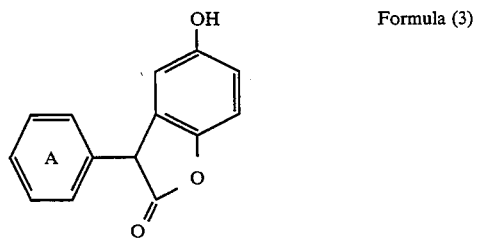

wherein:
$R^1$ and $R^2$ each independently is —H or alkyl;
$R^3$ is alkyl;
$R^4$ is —H or alkyl;
$R^5$ and $R^6$ each independently is alkyl; or
$R^5$ and $R^6$ together with the N atom to which they are attached form a heteroalicyclic ring; and
Ring A is unsubstituted or is substituted by from one to three substituents
provided that at least one of $R^1$, $R^2$ and $R^4$ is —H.

When any one of the groups represented by $R^1$, $R^2$, $R^3$, $R^4$, $R^5$ or $R^6$ is alkyl it preferably contains from 1 to 10 carbon atoms, more preferably from 1 to 6 carbon atoms and especially from 1 to 4 carbon atoms. The alkyl groups represented by $R^1$ to $R^6$ may be straight or branched chain alkyl groups and may be substituted by substituents selected from phenyl, halogen such as —Cl, —F and —Br, nitro, cyano, hydroxy, amino, alkylamino, dialkylamino, alkoxy, alkoxyalkoxy, alkoxycarbonyl, alkylcarbonyl, alkoxyalkoxycarbonyl, alkylcarbonyloxy and alkylcarbonylamino in which each alkyl is preferably $C_{1-4}$-alkyl and each alkoxy is preferably $C_{1-4}$-alkoxy.

Where $R^5$ and $R^6$ together with the N atom to which they are attached form a heteroalicyclic ring, the term heteroalicyclic ring means a saturated or partially unsaturated ring having at least one hetero i.e. non-carbon atom in the ring preferably morpholine or piperidine.

Where Ring A carries substituents these are preferably in the 4-position, or in the 3- and 4-positions, or in the 3-, 4- and 5-positions. Suitable substituents for Ring A may be independently selected from any of the substituents described above for the alkyl groups represented by $R^1$ to $R^6$ and preferably from $C_{1-4}$-alkyl, $C_{1-4}$-alkoxy, hydroxy, $C_{1-4}$-alkylcarbonylamino and halogen especially from $C_{1-4}$-alkyl, $C_{1-4}$-alkoxy and hydroxy.

The present process my be performed by stirring the reactants in a liquid medium, preferably in an acidic medium, more preferably in an acid organic medium, especially in an alkylsulphonic acid such as methanesulphonic acid, or an aliphatic carboxylic acid such as ethanoic acid, propanoic acid or butanoic acid, optionally containing another acid such as sulphuric acid or in an organic liquid, preferably a hydrocarbon such as toluene or a halogenated hydrocarbon such as chlorobenzene which contains an acid preferably an alkylsulphonic such as methanesulphonic acid, an alkanoic acid such as ethanoic acid or an arylsulphonic acid such as toluenesulphonic acid. The process is preferably carried out at a temperature from 0° C. to 150° C., more preferably at from 10° C. to 100° C. and especially at from 15° C. to 75° C. When the reaction is substantially complete, as judged by the disappearance of starting materials using a technique such as thin layer chromatography, the product may be isolated in any convenient manner for example by precipitation of the product from the reaction mixture by adding water and collecting the product by filtration.

According to a further feature of the present invention there is provided a compound of Formula (2) wherein $R^1$, $R^2$, $R^3$, $R^4$, $R^5$ and $R^6$ are as hereinbefore defined.

The compound of Formula (2) may be prepared by reaction of an aniline of Formula (4):

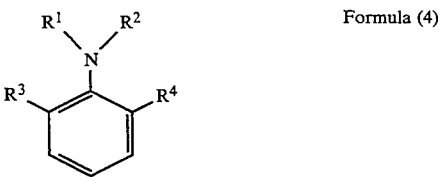

wherein: $R^1$, $R^2$, $R^3$ and $R^4$ are as hereinbefore defined, with glyoxylic acid and a compound of Formula (5):

wherein: $R^5$ and $R^6$ are as hereinbefore defined.

The process may be performed by warming a mixture of the reactants in a liquid medium, preferably in an organic liquid, more preferably in an alkanol, such as methanol or ethanol, a hydrocarbon such as toluene or a halogenated hydrocarbon such as chlorobenzene. The glyoxylic acid is preferably soluble in the liquid medium selected. The process is preferably carried out at a temperature from 0° C. to 120° C., more preferably from 10° C. to 100° C. and especially from 15° C. to 75° C. When the reaction is substantially complete, as judged by disappearance of starting material using a technique such as liquid chromatography, the product may be isolated by filtration from the reaction mixture.

The polycyclic dyes are useful for the coloration of synthetic textiles such as polyester to which they impart blue to navy shades.

The invention is further illustrated by the following Examples in which all parts and percentages are by weight unless otherwise indicated:

EXAMPLE 1

To a solution of glyoxylic acid monohydrate (5 parts) in methanol (30 parts), stirring in an ice bath, was added morpholine (4.7 parts). After cooling to ambient, 2-ethyl-6-methylaniline (7.3 parts) was added and the mixture was stirred under reflux for 3 hours. After cooling to ambient, the product was isolated by filtration, washed with methanol and dried to yield 1-morpholino-1-[4-amino-3-ethyl-5-methyl phenyl]-acetic acid (8.8 parts, 58%), m.p. 245° C. decomp.

EXAMPLE 2

To a solution of glyoxylic acid monohydrate (5 parts) in methanol (30 parts), stirring in an ice bath, was added piperidine (4.6 parts). After cooling to ambient, 2-ethyl-6-methylaniline (7.3 parts) was added and the mixture was stirred under reflux for 16 hours. After cooling to ambient, the reaction mixture was steam distilled to remove excess reactants and evaporated to dryness to yield 1-piperidino-1-[4-amino-3-ethyl-5-methylphenyl]-acetic acid (2.3 parts, 15%).

EXAMPLE 3

A mixture of 1-morpholino-1-[4-amino-3-ethyl-5-methylphenyl]-acetic acid (2 parts), 5-hydroxy-2-oxo-3-phenyl-2,3-dihydrobenzofuran (1.3 parts) and glacial acid (10 parts) was stirred under reflux for 1 hour. Methanol (20 parts) was added and the mixture was stirred at ambient for 18 hours. The product was isolated by filtration, washed with water and dried at 50° C. to yield 3-phenyl-7-[4-amino-3-ethyl-5-methylphenyl]-2,6- dioxo-2,6-dihydrobenzo[1:2-b,4:5-b']-difuran (0.28 parts, 13%), λmax (CH$_2$Cl$_2$)=580 nm.

EXAMPLE 4

The procedure of example 3 was repeated except that in place of the 5-hydroxy-2-oxo-3-phenyl-2,3-dihydrobenzofuran (1.3 parts) there were used, 5-hydroxy-2-oxo-3-(4-n-propoxyphenyl)-2,3-dihydrobenzofuran (1.3 parts), to yield 3-(4-n-propoxyphenyl)-7-(4-amino-3-ethyl-5- methylphenyl)-2,6-dioxo-2,6-dihydrobenzo[1:2-b,4:5-b']-difuran (0.4 parts), λmax=586 nm (CH$_2$Cl$_2$).

EXAMPLE 5

The procedure of example 3 was repeated except that in place of the 5-hydroxy-2-oxo-3-phenyl-2,3-dihydrobenzofuran (1.3 parts) there were used, 5-hydroxy-2-oxo-3-(4-methylphenyl)-2,3-dihydrobenzofuran (1.3 parts), to yield 3-(4-methylphenyl)-7-(4-amino-3-ethyl-5-methylphenyl)-2,6-dioxo-2,6-dihydrobenzo[1:2-b, 4:5-b']-difuran (0.3 parts), λmax=581 nm (CH$_2$Cl$_2$).

EXAMPLE 6

The procedure of example 3 was repeated except that in place of the 5-hydroxy-2-oxo-3-phenyl-2,3-dihydrobenzofuran (1.3 parts) there were used, 5-hydroxy-2-oxo-3-(4-acetylaminophenyl)-2,3-dihydrobenzofuran (1.5 parts), to yield 3-(4-acetylaminophenyl)-7-(4-amino-3-ethyl-5-methylphenyl)-2,6-dioxo-2,6-dihydrobenzo[1:2-b,4:5-b']-difuran (0.4 parts), λmax=576 nm (CH$_2$Cl$_2$).

EXAMPLE 7

The procedure of example 3 was repeated except that in place of the 5-hydroxy-2-oxo-3-phenyl-2,3-dihydrobenzofuran (1.3 parts) there were used, 5-hydroxy-2-oxo-3-(4-chlorophenyl)-2,3-dihydrobenzofuran (1.4 parts), to yield 3-(4-chlorophenyl)-7-(4-amino-3-ethyl-5-methylphenyl)- 2,6-dioxo-2,6-dihydrobenzo[1:2-b,4:5-b']-difuran (0.3 parts), λmax=578 nm (CH$_2$Cl$_2$).

EXAMPLE 8

The procedure of example 3 was repeated except that in place of the 5-hydroxy-2-oxo-3-phenyl-2,3 -dihydrobenzofuran (1.3 parts) there were used, 5-hydroxy-2-oxo-3-(4-hydroxyphenyl)-2,3-dihydrobenzofuran (1.3 parts), to yield 3-(4-hydroxyphenyl)-7-(4-amino-3-ethyl-5-methylphenyl)-2,6-dioxo-2,6-dihydrobenzo[1:2-b,4:5-b']-difuran (0.2 parts), λmax=582 nm (CH$_2$Cl$_2$).

EXAMPLE 9

The procedure of example 3 was repeated except that in place of the 5-hydroxy-2-oxo-3-phenyl-2,3-dihydrobenzofuran (1.3 parts) there were used, 5-hydroxy-2-oxo-3-(3-chloro-4-hydroxyphenyl)-2,3-dihydrobenzofuran (1.5 parts), to yield 3-(3-chloro-4-hydroxyphenyl)-7-(4-amino-3-ethyl-5-methylphenyl)-2,6-dioxo-2,6-dihydrobenzo[1:2-b,4:5-b']-difuran (0.4 parts), λmax=585 nm (CH$_2$Cl$_2$).

EXAMPLE 10

The procedure of example 2 was repeated except that in place of piperidine (4.6 parts) there were used, dimethylamine (2.5 parts), to yield 1-dimethylamino-1-(4-amino-3-ethyl-5-methylphenyl)-acetic acid, (1.9 parts).

EXAMPLE 11

The procedure of example 2 was repeated except that in place of piperidine (4.6 parts) there were used, diethylamine (4.0 parts), to yield 1-diethylamino-1-(4-amino-3-ethyl-5-methylphenyl)-acetic acid,(1.4 parts).

EXAMPLE 12

The procedure of example 2 was repeated except that in place of piperidine (4.6 parts) there were used, dibutylamine (7.0 parts), to yield 1-dibutylamino-1-(4-amino-3-ethyl-5-methylphenyl)-acetic acid,(2.1 parts).

EXAMPLE 13

The procedure of example 2 was repeated except that in place of piperidine (4.6 parts) there were used, 4-methylpiperidine (5.4 parts), toyield1-(4-methylpiperidino)-1 -(4-amino-3-ethyl-5-methylphenyl)-acetic acid, (1.4 parts).

EXAMPLE 14

The procedure of example 3 was repeated except that in place of the 1-morpholino-1-(4-amino-3-ethyl-5-methylphenyl)-acetic acid (2 parts) there were used, 1-piperidino-1-(4-amino-3-ethyl-5-methylphenyl) acetic acid (2 parts) to yield 3-phenyl-7-(4-amino-3-ethyl-5-methylphenyl)-2,6-dioxo-2,6-dihydrobenzo[1:2-b,4:5-b']-difuran (0.35 parts), λmax=580 nm (CH₂Cl₂).

EXAMPLE 15

The procedure of example 3 was repeated except that in place of the 1-morpholino-1-(4-amino-3-ethyl-5-methylphenyl)-acetic acid (2 parts) there were used, 1-dimethylamino-1-(4-amino-3-ethyl-5- methylphenyl)-acetic acid (1.9 parts) to yield 3-phenyl-7-(4-amino-3 ethyl-5-methylphenyl)-2,6-dioxo-2,6-dihydrobenzo[1:2-b,4:5-b']-difuran (0.25 parts), λmax=580 nm (CH₂Cl₂).

EXAMPLE 16

The procedure of example 1 was repeated except that in place of the 2-ethyl-6-methylaniline (7.3 parts) there were used, 2,6-dimethylaniline (6.5 parts) to yield 1-morpholino-1(4-amino-3,5- dimethylphenyl)-acetic acid (8.1 parts).

EXAMPLE 17

The procedure of example 1 was repeated except that in place of the 2-ethyl-6-methylaniline (7.3 parts) there were used, 2-butyl-6-methylaniline (8.8 parts) to yield 1-morpholino-1-(4-amino-3-butyl-5- methylphenyl)-acetic acid (9.3 parts).

We claim:

1. A process for the preparation of a polycyclic dye of Formula (1).

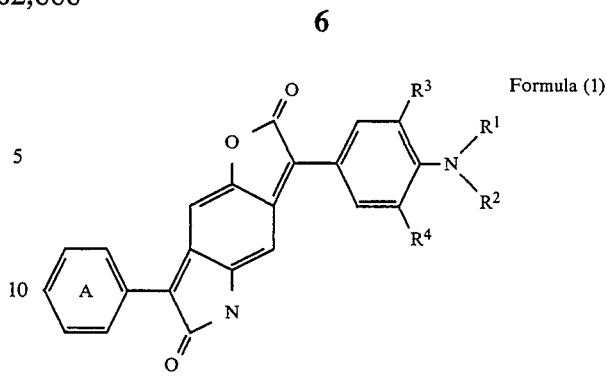
Formula (1)

by reacting a compound of Formula (2):

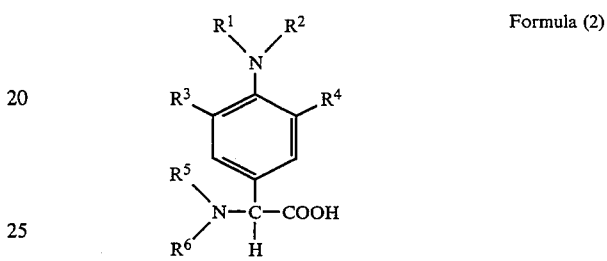
Formula (2)

with a benzofuranone of Formula (3):

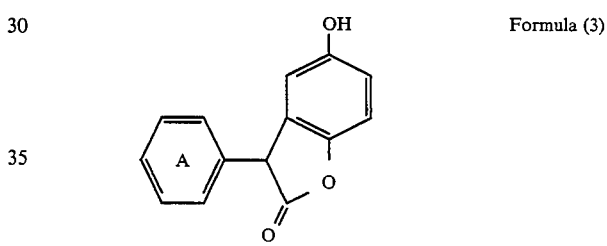
Formula (3)

wherein:
$R^1$ and $R^2$ each independently is —H or alkyl;
$R^3$ is alkyl;
$R^4$ is —H or alkyl;
$R^5$ and $R^6$ each independently is alkyl; or
$R^5$ and $R^6$ together with the N atom to which they are attached form a heteroalicyclic ring; and
Ring A is unsubstituted or is substituted by from one to three substitutents independently selected from $C_{1-4}$-alkyl, $C_{1-4}$-alkoxy, hydroxy, $C_{1-4}$-alkylcarbonylamino and halogen,
provided that at least one of $R^1$, $R^2$ and $R^4$ is —H.

* * * * *

UNITED STATES PATENT AND TRADEMARK OFFICE
CERTIFICATE OF CORRECTION

PATENT NO. : 5,362,888

DATED : November 8, 1994

INVENTOR(S) : Nigel Hall et al

Page 1 of 2

It is certified that error appears in the above-indentified patent and that said Letters Patent is hereby corrected as shown below:

ON THE TITLE PAGE:

[57] ABSTRACT

Col. 1, lines 10-22, Formula (1); and

Col.6, lines 1-13, Formula (1), change Formula (1) from

" 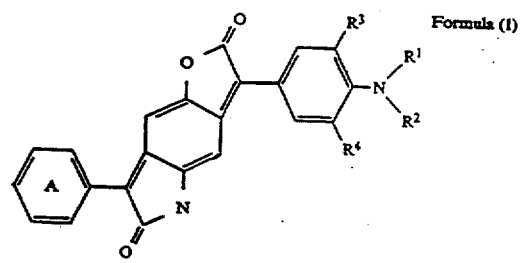 "

UNITED STATES PATENT AND TRADEMARK OFFICE
CERTIFICATE OF CORRECTION

PATENT NO. : 5,362,888

DATED : November 8, 1994

INVENTOR(S) : Nigel Hall et al

Page 2 of 2

It is certified that error appears in the above-indentified patent and that said Letters Patent is hereby corrected as shown below:

to

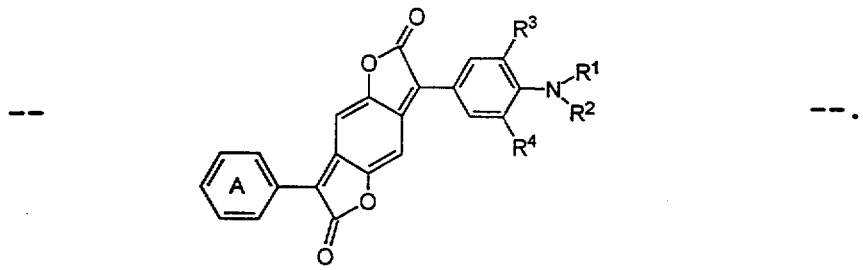

--.

Signed and Sealed this

Twentieth Day of June, 1995

Attest:

BRUCE LEHMAN

Attesting Officer

Commissioner of Patents and Trademarks